United States Patent
Huang (10) Patent No.: US 10,251,837 B2
(45) Date of Patent: Apr. 9, 2019

(54) COMPOSITIONS FOR NANOEMULSION DELIVERY SYSTEMS

(71) Applicant: Jingjun Huang, Monmouth Junction, NJ (US)

(72) Inventor: Jingjun Huang, Monmouth Junction, NJ (US)

(73) Assignee: Jingjun Huang, Monmouth Junction, NJ (US)

( * ) Notice: Subject to any disclaimer, the term of this patent is extended or adjusted under 35 U.S.C. 154(b) by 0 days.

(21) Appl. No.: 14/623,150

(22) Filed: Feb. 16, 2015

(65) Prior Publication Data

US 2015/0231070 A1    Aug. 20, 2015

Related U.S. Application Data

(60) Provisional application No. 61/939,965, filed on Feb. 14, 2014.

(51) Int. Cl.
| | | |
|---|---|---|
| *A61K 9/107* | (2006.01) | |
| *A61K 47/24* | (2006.01) | |
| *A61K 38/13* | (2006.01) | |
| *A61K 47/26* | (2006.01) | |
| *A61K 47/44* | (2017.01) | |

(52) U.S. Cl.
CPC ............ *A61K 9/1075* (2013.01); *A61K 38/13* (2013.01); *A61K 47/24* (2013.01); *A61K 47/26* (2013.01); *A61K 47/44* (2013.01)

(58) Field of Classification Search
None
See application file for complete search history.

(56) References Cited

U.S. PATENT DOCUMENTS

| | | |
|---|---|---|
| 8,298,569 B2 | 10/2012 | Philips et al. |
| 2005/0048013 A1 | 3/2005 | Diec et al. |
| 2008/0138296 A1 | 6/2008 | Tamarkin et al. |
| 2010/0305218 A1 | 2/2010 | Wooster et al. |
| 2011/0045050 A1* | 2/2011 | Elbayoumi .......... A61K 9/1075 424/423 |
| 2012/0045489 A1* | 2/2012 | Tong .................... A61K 9/0019 424/400 |

OTHER PUBLICATIONS

PCT/US2015/016035; International Search Report and Written Opinion; dated May 21, 2015; 7 pgs.

* cited by examiner

*Primary Examiner* — Jeffrey T. Palenik
(74) *Attorney, Agent, or Firm* — Gearhart Law LLC (57) ABSTRACT

The present disclosure provides a pharmaceutically acceptable, stable, and optically clear oil-in-water nanoemulsions (intensity-averaged diameter<100 nm) with an oil phase comprising>10% w/v of long chain triglyceride, total surfactant and cosurfactant concentration less than that of oil phase and without the use of alcohol as cosolvent in the aqueous phase. The nanoemulsions of this disclosure have extremely favorable particle size distribution, optical clarity, and product stability against Ostwald ripening with high levels of oil concentrations. Poorly water soluble, therapeutically active agents and others can be incorporated in the nanoemulsion systems to improve their solubility/stability in aqueous medium or to enhance their delivery for use in pharmaceutical, food, cosmetic, and other applications by oral, intravenous, subcutaneous, intra muscular, inhalation, nasal, topical, ocular, and transdermal routes.

21 Claims, 6 Drawing Sheets

COMPOSITIONS FOR NANOEMULSION DELIVERY SYSTEMS

PRIORITY

This application claims priority of U.S. provisional application No. 61/939,965 filed on Feb. 14, 2014 the contents of which is incorporated by reference its entirety.

FIELD OF INVENTION

The present invention relates to compositions of stable, and optically clear, oil-in-water nanoemulsions with intensity-averaged diameter less than 100 nm, comprising an oil phase with at least 10% w/v long chain triglyceride and eliminating the need of alcohol in the aqueous phase as a cosolvent. The processes for the said compositions and their applications as a carrier for active components in pharmaceutical, food, nutraceutical, and cosmetic industries are described in the invention.

BACKGROUND

Drug's low solubility constitute a very difficult challenge to develop a bioavailable and physical stable pharmaceutical and nutraceutical product, particularly when intravenous or oral solutions are needed. A number of approaches for preparing intravenous and oral liquid compositions of sparingly or poorly water-soluble basic drugs are available. These methods include micellar solubilization or drug nanoparticle suspension by means of surface-active agents; formation of complexes with cyclodextrin and its derivatives (Hydroxypropyl beta-Cyclodextrin (HPBCD) and sulfobutylether-β-cyclodextrin (SBECD)); use of various co-solvent systems; and formation of salt with strong acid with a low solution pH. However, for micellar system, surfactants have been implicated by adverse effects such as irritation, hemolysis and histamine reaction and severe anaphylaxis reaction, and for nanosuspension system wherein pure drug particles of nanosize stabilized by polymer and surfactants, potential catalytic degradation of drug substance due to higher exposure area to aqueous media and the surrounding surfactants has been reported; taste masking and injection pain is another issue for the micellar/nanosuspension system due to a higher concentration of free drug available in the aqueous medium; co-solvent systems are known for causing precipitation, injection pain and phlebitis; potential nephrotoxicity and bradycardia and reduction of blood pressure caused by cyclodextrin and its derivatives and the potential concerns of cyclodextrin binding with co-administered lipophilic drugs have been reported; and the low solution pH of weakly basic salt formed with strong acid will cause drug-excipient and product stability issue and cause tasting issue, injection site irritation and pain as a result of precipitation of the drug as free base when contact with blood at neutral pH. In summary, each of these methods listed above has its inherent limitations and are insufficient to formulate low soluble drugs in a biocompatible vehicle having sufficient stability, minimum side effects, and appropriate pharmadynamic profiles as either intravenous, ocular, nasal, topical, transdermal, or oral administration.

Oil-in-water emulsions, which are made of oil droplets dispersed in an aqueous continuous phase, offers a unique system that can address drug solubility and stability problems with many applications in products such as pharmaceutical, food, and cosmetics. One of the uses of emulsions is to deliver active pharmaceutical ingredients and active components for use in topical, nutraceutical, oral, nasal, ocular, and pharmaceuticals. Active components that are soluble in oil can be dissolved/dispersed within the oil phase of the emulsion, and active components that are poorly soluble in both oil and water can be incorporated at the interfacial region of the emulsion as well.

Based on its appearance or particle size, emulsion can be classified into three types: macroemulsion, microemulsion and nanoemulsion. Macroemulsion with average size range of >100 nm tend to have a cloudy milky appearance because the many interfaces scatter light as it passes through the emulsion. Microemulsions and nanoemulsions, with average droplet sizes below 100 nm are two special classes of emulsions, appearing optically clear (translucent or transparent). This property is due to the fact that light are scattered by the droplets only if their sizes exceed about one-quarter of the wavelength of the incident light. When the mean droplet size in the emulsion is below about 100 nm, preferably below 70 nm, the light can penetrate through the emulsion without being scattered. Microemulsions are thermodynamic stable system, spontaneously formed by "solubilizing" oil molecules with a mixture of surfactants, co-surfactants, and co-solvents. Whereas nanoemulsion are thermodynamic metastable system, formation of which require external energy to break down oil droplet to below 100 nm level.

Conventional oil in water emulsions, i.e. macroemulsion, are inherently unstable system and will not form spontaneously. Energy input such as mechanical mixing, homogenizing, or ultrasound is required to form a macroemulsion; and macroemulsions tend to revert back to the stable state of the phases resulting phase separation such as agglomeration and creaming. Besides physical instability, relative large droplet size of macroemulsions have a lower interfacial area to volume ratio that limit the ability of macroemulsion to efficiently dissolve poorly soluble compounds, which are soluble either inside oil or at the oil-water interface; and the opacity of macroemulsion reduce visual clarity when administration to eyes. Furthermore, the release of the active ingredient from macroemulsions comprised of long chain triglyceride oil by oral administration maybe be often limited by the rate and extent of lipolysis. The rate of triglyceride emulsion digestion in GI tract is a function of pH, lipase concentration, bile salt and emulsion surface area. Emulsions with higher surface area to volume ratios would undergo faster lipolysis than those with low surface area to volume ratios.

Formulations of emulsion into average size below 100 nm are exceptions to those disadvantages, wherein microemulsions are thermodynamically stable, and nanoemulsions, though thermodynamically metastable in nature, could still maintain its kinetic stability for a long time period due to extremely small size. The formation of emulsions below 100 nm has added benefits of increasing the relative amount of interfacial area considerably. An increase in the relative amount of interfacial area can lead to a greater ability to dissolve poorly soluble active components into the aqueous medium and a faster rate of digestion by lipolysis as compared to macro emulsions and thus a faster release of the active ingredient from the oil droplets. Due to small size below 100 nm, microemulsion or nanoemulsion has added benefit of aiding active compounds to penetrate epithelial mucosal layers such as eyes, skin, nasal, lung, GI tract, tumor, blood vein, and blood-brain barrier.

Despite of the similarity in particle size less than 100 nm and performance in delivery of active compounds, microemulsions and nanoemulsions are fundamentally different.

Despite of its thermodynamic stability, the required surfactant concentration for a microemulsion system significantly exceeds the concentration of the oil phase and is normally several times higher than that of nanoemulsion. Because of many undesirable side-effects caused by surfactants and due to the government regulations of daily intake limits of many surfactants, microemulsions are disadvantageous in many pharmaceutical applications such as intravenous, ocular, and oral administration as compared to nanoemulsions. In addition, many surfactants have a bitter taste when present in the foods/dosage form, which may cause palatability issues. Furthermore, the physical stability of a microemulsion system is often affected by dilution, by heating, or by changing pH levels.

A nanoemulsion—even though it will not be formed spontaneously and only maintain a kinetic stability—uses much less surfactant due to the aid of mechanic shear to break down oil droplets to nanosize level in the presence of water and surfactant. This leads to a more tolerable system from a toxicological and regulatory perspective. Similarly as microemulsions, nanoemulsions can have the benefit of appearing translucent as a result of their small size. Nanoemulsions have the same high interfacial area to volume ratio as microemulsions, which can aid in the dissolution of poorly soluble compounds and aid in the rapid digestion of the emulsion by lipolysis. In contrast to microemulsions, nanoemulsions maintain its physical stability upon dilution and/or change in pH.

Despite of many advantages over macroemulsion and microemulsions, nanoemulsions have its limitations, i.e. kinetic stability—the particle size may increase over time via Ostwald ripening. An increase in nanoemulsion particle size over time is disadvantageous as the nanoemulsion will lose its clarity accompanied with a corresponding decrease in interface surface area. In order to achieve stable nanoemulsion with average particle size below 100 nm, low viscosity oils including short chain triglycerides or medium chain triglycerides such as Migloyol are often utilized to make nanoemulsion, the disadvantage of which is the tendency of Ostwald ripening due to smaller molecular size, high aqueous solubility and low viscosity of short/medium chain triglycerides. To improve physical stability of nanoemulsion, long chain triglycerides with very low aqueous solubility may be employed. However, it is known that the large molecular volume and high viscosity of long chain triglycerides prevents them from readily forming optically clear (transparent or translucent) nanoemulsions with a high level of oil content. Therefore, in order to form translucent nanoemulsion comprising long chain triglyceride, either high level of small molecule weight organic cosolvent such as alcohol, or higher levels of toxic surfactants such as Cremophor EL relative to that of oil phase, are commonly utilized to reduce the surface tension of the oil droplets comprising long chain triglyceride. This, however may lead to an intolerable system from safety, toxicological, regulatory perspective. For example, since phosphatidylcholines (egg or soy lecithin) are naturally occurring non-toxic, biocompatible surfactants, the preparation of lecithin-based emulsions is of considerable pharmaceutical interest. However, since lecithin has a strong tendency to form liquid crystalline structures at a relatively low concentration, particularly in water phase, adding alcohol to the aqueous phase as a cosolvent is necessary in order to reduce the interfacial tension thus to produce lecithin-based microemulsion/nanoemulsion comprising long chain triglyceride oils. However, alcohol is known to induce toxic side effects such as enzyme induction, drug-drug interaction, or damage to central nerve system.

Therefore, challenges remain in creating nanoemulsion with its oil phase comprising long chain triglyceride with a high level of oil content of the composition, wherein the emulsion has an average size of less than 100 nm (intensity averaged), maintains good stability against Ostwald ripening and optical translucency, uses biocompatible surfactant and relative low level of other surfactants, and eliminate the use of undesirable alcohol as co-solvent in the aqueous phase. The creation of such nanoemulsions would have advantages in improving emulsion product safety, efficacy, stability, tolerability, and taste.

SUMMARY OF INVENTION

To address the above mentioned flaws and problems in the current art, there is a need in the art for an optically clear nanoemulsion system with its oil phase comprising at least 10% w/v of long chain triglyceride, which has an intensity-averaged droplet size of less than 100 nm and good stability against Ostwald ripening, uses biocompatible surfactant and low level of other surfactants (<15%), and eliminates the use of undesirable alcohol as a co solvent in the aqueous phase.

Considering the aforementioned problems, the present disclosure provides a surprising result that aqueous-based oil/water nanoemulsion compositions with intensity-average mean droplet size of <100 nm, unexpectedly gives extremely favorable particle size distribution, optical clarity, and product stability against Ostwald ripening with the oil phase concentration up to 50% of the composition. Poorly water soluble, therapeutically active agents and others can be incorporated into the nanoemulsion systems to improve their solubility and stability in aqueous medium and for active component delivery.

It is an object of this invention to provide a stable optically clear oil/water nanoemulsion comprising and oil phase comprising long chain triglycerides and/or other oils; and ionizable surfactant and co surfactant(s); an aqueous phase containing no alcohol as a co solvent; and a pH adjusting agent.

The oil phase of the emulsion composition is at least of 0.5-50% w/v of the composition, comprising >10% of long chain triglyceride in the oil phase.

The ionizable surfactant is a biocompatible ionizable surfactant or its derivative such as egg or soy lecithin in combination with pharmaceutical acceptable co-surfactant(s). The total surfactant and cosurfactant concentration is <25% w/v of the composition where the ratio of surfactant to cosurfactant is in the range of 10:0.1 to 0.1:10, 10:1 to 1:10, 10:1 to 1:5, or 5:1 to 1:5, and total concentration of surfactant and co surfactant is less than 100% w/w of the oil phase.

The aqueous phase comprises water and contains no alcohol as the co solvent.

It is another object of this invention to provide a method to make a stable, optically clear, oil/water nanoemulsion composition comprising long chain triglyceride with intensity-averaged oil droplets <100 nm and without the use of alcohol as co-solvent in the aqueous phase, said method comprising the steps of: a) preparing an oil phase comprising long chain triglyceride; b) preparing an aqueous phase comprising water and pH adjustment agent; c) incorporating biocompatible surfactant and co-surfactant(s) either in the oil phase or in the aqueous phase; d) dispersing the oil phase in the aqueous phase to form a coarse emulsion; e) forming a final emulsion by sonicating or high pressure homogenizing the emulsion of step d); and f) adjusting pH.

It is yet another object of this invention is to provide a method to use the optically clear nanoemulsion system composition in treatment of a human or an animal, where the composition comprises long chain triglyceride with intensity-averaged oil droplets <100 nm and without using alcohol as the organic cosolvent for therapeutic agents and others for use in pharmaceutical, food, cosmetic, and other applications by oral, intravenous, subcutaneous, intra muscular, inhalation, nasal, topical, ocular, and transdermal routes, with such stability and purity to meet the requirements of the applicable compendium, the Food and Drug Administration, and GMP. Said method comprises the steps of: a) providing in a liquid form of an oil/water nanoemulsion composition prepared by dispersing/dissolving therapeutic active agent or other agents in an oil carrier; b) preparing an aqueous phase comprising water and pH adjustment agent; c) dispersing the oil phase into the aqueous phase by sonicating or homogenizing to form oil droplets; and d) administering the said nanoemulsion composition to human or animals.

It is yet another object of this invention to provide a method to treat a human or an animal by using a optically clear nanoemulsion system composition comprising long chain triglyceride with intensity-averaged oil droplets <100 nm and without using alcohol as an organic cosolvent for therapeutic agents and others for use in pharmaceutical, food, cosmetic, and other applications by oral, intravenous, subcutaneous, intra muscular, inhalation, nasal, topical, ocular, and transdermal routes, with such stability and purity to meet the requirements of the applicable compendium, the Food and Drug Administration, and GMP. The method comprises the steps of: a) providing in a liquid form of an oil/water nanoemulsion composition prepared by dispersing the oil phase into the aqueous phase by sonicating or homogenizing to form nanoemulsion; b) adding therapeutic active agent or others agents into the oil/water nanoemulsion from step a) and mixing to dissolve the therapeutic active agent or others agents into the oil phase; and c) administering the said nanoemulsion composition to human or animals.

It is yet another object of this invention to provide a method to use the optically clear nanoemulsion system composition for treating a human or an animal where the composition comprises long chain triglyceride with intensity-averaged oil droplets <100 nm and without using alcohol as an organic cosolvent for therapeutic agents and others for use in pharmaceutical, food, cosmetic, and other applications by oral, intravenous, subcutaneous, intra muscular, inhalation, nasal, topical, ocular, and transdermal routes, with such stability and purity to meet the requirements of the applicable compendium, the Food and Drug Administration, and GMP. The method comprises the steps of: a) providing in a liquid form of an oil/water coarse emulsion composition prepared by dispersing the oil phase into the aqueous phase to form coarse emulsion; b) Adding therapeutic active agent or others agents into the oil/water coarse emulsion from step a), and mixing to dissolve/disperse the therapeutic active agent or others agents into the oil phase; c) obtaining a liquid form of an oil/water nanoemulsion by sonicating or homogenizing; and d) administering the said nanoemulsion composition to human or animals.

DETAILED DESCRIPTION OF THE INVENTION

The term of "emulsion" is defined as a system (as fat in milk) consisting of a liquid dispersed with or without an emulsifier in an immiscible liquid usually in droplets of larger than colloidal size.

The term of "oil in water emulsion" refers to an emulsion system, which is made of oil droplets dispersed in an aqueous continuous phase. In this disclosure, the term of "emulsion" refers to oil in water emulsion without exception.

The term of "microemulsion" is defined as dispersion made of water, oil, and surfactant(s) that is an isotropic and thermodynamically stable system with dispersed domain diameter varying approximately from 1 to 100 nm, usually 10 to 50 nm. The droplet size is the Z-average or intensity weighted average size as measured by dynamic light scattering. In this disclosure, the term of "microemulsion" refers to oil in water emulsion without exception.

The term of "nanoemulsion" is defined as dispersion made of water, oil, and surfactant(s) that is thermodynamically metastable system with dispersed domain diameter varying approximately from 1 to 100 nm, usually 10 to 50 nm. The droplet size is the Z-average or intensity weighted average size as measured by dynamic light scattering. In the said invention, the term of "nanoemulsion" refers to oil in water emulsion without exception.

The term of "medium chain triglyceride" means medium-chain (6 to 12 carbons) fatty acid esters of glycerol.

The term of "long chain triglyceride" means long-chain (>12 carbons) fatty acid esters of glycerol.

The term of "surfactant" means usually organic compounds that are amphiphilic, meaning they contain both hydrophobic groups and hydrophilic groups.

The term of "ionizable surfactant" means usually organic compounds that are amphiphilic, meaning they contain both hydrophobic groups and hydrophilic groups, and its head group can be ionized at physiological pH range of below 10.

The term of "cosurfactant" is a surfactant that acts in addition to another surfactant, further reducing the surface tension of a liquid.

The term of "cosolvent" is organic solvent that acts in addition to other solvent, further reducing the surface tension of a liquid.

The term of "transparent" is the physical property of allowing light to pass through the material without being scattered. It follows Snell's law; In other words, a transparent medium allows the transport of light and allows for image formation.

The term of "translucent" means a super-set of transparency: it allows light to pass through, but does not necessarily follow Snell's law; In other words, a translucent medium allows the transport of light but not allows for image formation.

The term of "optically clear" refers to either transparent or translucent for this invention.

The invention provides aqueous-based oil in water nanoemulsion formulation composition with mean droplet size (intensity-average, nm) of <100 nm, comprising an oil phase, a mixture of ionizable surfactant and co-surfactant, and an aqueous liquid carrier. The formulation if this invention comprises:

a) an oil phase comprising long chain triglyceride and/or other oil,
b) a mixture of ionizable surfactant and cosurfactant
d) an aqueous phase comprising water, pH adjustment agent and without alcohol as cosolvent.

Optionally, the emulsion formulation may also contain active component(s) for pharmaceutical, nutraceutical, food and cosmetic application, chelate agent, antioxidant, osmotic agent, suspending agent, preservative, and buffering agent. In some embodiments, the formulation further comprises a solubilizing agent, a flavoring agent, a sweetening agent, a viscosity inducing agent, electrolyte, another therapeutic agent, or a combination thereof.

Combinations of the various upper and lower limits to components of the nanoemulsion, as set forth in this disclosure, can be used to provide different embodiments of the invention.

According to one embodiment of this invention the nanoemulsion comprises:
a) at least 0.5-50% w/w of oil phase, which comprise long chain triglyceride
b) ionizable surfactant of 0.01-30% w/w;
d) co-surfactant of 0.01-30% w/w; and
d) 50-99% w/w of water.
in which the oil droplets have an intensity average size of less than 100 nm and the ratio of ionizable surfactant to co surfactant is in the range from 10:0.1 to 0.1:10, 10:1 to 1:10, 10:1 to 1:5, or 5:1 to 1:5, and the ratio of total surfactant/cosurfactant to oil is less than 1:1.

In a preferred embodiment, the oil-in-water nanoemulsion comprises 0.5-50 w/v % of an oil phase comprising at least 10% w/w long chain triglyceride in the oil phase, 0.1-30% of ionizable surfactant, 0.01-30% of cosurfactant and an aqueous phase without using alcohol as cosolvent in the external phase.

Oil phases in the emulsion may be a liquid or solid fat of animals, or vegetables, or of algal or synthetic origin. Those of animal origin include oils or fats such as fish oil, cod liver oil, blubber, lard, tallow, schmaltz, and butter fat. Those of vegetable origin include oils such as canola oil, castor oil, cocoa butter, coconut oil, coffee seed oil, corn oil, cotton seed oil, evening primrose oil, grapeseed oil, flax seed oil, menhaden oil, mustard seed oil, olive oil, palm oil, palm kernel oil, peanut oil, poppy seed oil, rapeseed oil, rice bran oil, safflower oil, sesame oil, soybean oil, sunflower oil, palm kernel oil, hazelnut oil, sesame oil and wheat germ oil. Those of synthetic origin include oils such as synthetic triglycerides, fractionated triglycerides, modified triglycerides, hydrogenated triglycerides or partially hydrogenated and mixtures of triglycerides are also included.

Preferably oil phases in the emulsion are a pharmaceutical-grade oil, preferably triglycerides such as, but not limited to soy bean oil, safflower seed oil, olive oil, cottonseed oil, sunflower oil, fish oil (containing the omega-3 fatty acids eicosapentaenoic acid (EPA), and docosahexaenoic acid (DHA)), castor oil, sesame oil, peanut oil, corn oil, medium chain triglycerides (such as Miglyol 812 or 810), and short chain triglyceride. The oil phase may also contain surfactant and/or co-surfactant such as egg lecithin, soy lecithin, and other phosphorus lipids, propylene glycol diesters, oleic acid, or monoglycerides (such as acetylareal monoglycerides). The oil phase may also be a mixture of said ingredients thereof.

The preferred lipid phase is soy bean oil, medium chain triglycerides (MCT), olive oil, and fish oil, either alone or mixture with others.

The most preferred oil phase is soy bean oil. The preferred range of oil carrier is 0.5-50%. The most preferred rang of oil carrier is 5-20%.

Surfactants are any pharmaceutically acceptable ionizable surfactant, preferably phospholipids extracted from egg yolk or soy bean, synthetic phosphatidyl cholines or purified phosphatidyl cholines from vegetable origin. Hydrogenated derivatives, such as phosphatidyl choline hydrogenated (egg) and phosphatidyl choline hydrogenated (soy) may also be used.

The most preferred surfactant is egg lecithin. The preferred range of surfactant is 0.35-30%. The most preferred range of surfactant is 1-18%.

The nanoemulsion may also contain a co-surfactant that acts synergistically with the ionizable surfactant to alter the interfacial tension permitting nanoemulsion formation.

Co-surfactants may be any pharmaceutically acceptable surfactants including but not limited to non-ionic surfactants such as poloxamers (for example Poloxamer 188 and 407), poloxamines, polyoxyethylene stearates, polyoxyethylene sorbitan fatty acid esters or sorbitan fatty acid esters and ionic surfactants may also be used such as cholic acid and deoxycholic acid or surface active derivatives or salts thereof. The co-surfactant may also be selected from the group consisting of oleic acid, sodium oleate, cholic acid, sodium cholate, deoxycholic acid, deoxysodium cholate and a mixture thereof. Alcohol is excluded for use as cosurfactant or cosolvent in the external aqueous phase. The co-surfactant is presented in the emulsion of this disclosure in the range of 0.01-30 w/v % of the composition. The ratio of surfactant to cosurfactant is in the range of 10:0.1 to 0.1:10, 10:1 to 1:10, 10:1 to 1:5, or 5:1 to 1:5.

The preferred range of aqueous phase is 50-99%.

The emulsion formulation may also contain active component(s) for pharmaceutical, nutraceutical, food and cosmetic application, chelate agent, antioxidant, osmotic agent, suspending agent, preservative, and buffering agent. In some embodiments, the emulsion may also contain solubility enhancers (excluding alcohol), chelate agent, preservative, antioxidants, stabilizers, suspending agent, pH-adjusting agents or tonicity modifying agents, such as glycerol, polymer as suspending agent, and sweetener, etc. Stabilizers may be pH modifying agents, anti-creaming or anti-foaming agents or agents which impart stability to the nanoemulsion.

The amount of active component in the nanoemulsion may be 0 to 50%.

The amount of other ingredient besides the active component in the nanoemulsion may be 0.5 to 50 wt %.

Desirable emulsions are stable systems of intensity-average mean droplet size of <100 nanometer with optically clear (transparent or translucent). The preferred intensity-average mean droplet size is below 100 nm nanometer; the most preferred intensity-average droplet size is below 75 nanometer.

The preferred pH range of the emulsion after manufacturing and during storage is below pH 10. The pH adjustment agent can be a buffer or sodium hydroxide or other pH adjustment agents or combination thereof.

The emulsion of the invention can be prepared in the following method: For the aqueous phase, water is dispensed to a container and heated to about 40-80° C. and pH is adjusted to 1-10. For the oil phase, oil is dispensed into another container and heated to about 40-80° C. Surfactant and co-surfactant is then added to the oil and heated to about 40° C. to about 80° C. Optionally, surfactant/cosurfactant can be added to the aqueous phase. The aqueous and oil phases are then mixed together by a high shear mixer to form a coarse emulsion. The emulsion is then sonicated or homogenized with a high pressure homogenizer or a microfluidizer at a pressure of about 5000-30,000 psi and a temperature range of about 5° C. to about 70° C. until a nanoemulsion with a desired droplet size is obtained. The pH is adjusted with pH adjustment agent such as sodium hydroxide to the final pH. The samples are filtered and dispensed into containers, often with nitrogen gas overlay and capped with stoppers. The product can be manufactured by an aseptic process or by terminal sterilization. Preferably the dosage units are autoclaved to get sterile and stable emulsions. In one embodiment, the emulsion was autoclaved at 121° C. for 15-20 minutes. In another embodiment, the emulsion is processed aseptically under sterile environment without autoclave.

One embodiment of this invention is a method to make nanoemulsion with added active component for use in human or animal treatment, the method comprising the steps of: a) providing in a liquid form of an oil/water nanoemulsion composition prepared by i) Adding therapeutic active agent or others agents into the oil and mixing to dissolve the therapeutic active agent or others agents into the oil phase; ii) dispersing the oil phase comprising active component into the aqueous phase by sonicating or homogenizing to form nanoemulsion; and b) administering the said nanoemulsion composition to human or animals.

One embodiment of this invention is a method to make nanoemulsion with added active component for use in human or animal treatment, said method comprising the steps of: a) providing in a liquid form of an oil/water nanoemulsion composition prepared by i) dispersing the oil phase into the aqueous phase by sonicating or homogenizing to form nanoemulsion; ii) Adding therapeutic active agent or others agents into the oil/water nanoemulsion from step a) and iii) mixing to dissolve the therapeutic active agent or others agents into the oil phase; and b) administering the said nanoemulsion composition to human or animals.

Another embodiment this invention is to provide a method to make nanoemulsion with added active component for use in human or animal treatment, said method comprising the steps of a) providing in a liquid form of an oil/water coarse emulsion composition prepared by i) dispersing the oil phase into the aqueous phase to form coarse emulsion; ii) Adding therapeutic active agent or others agents into the oil/water coarse emulsion from step i), and iii) mixing to dissolve/disperse the therapeutic active agent or others agents into the oil phase; iv) obtaining a liquid form of an oil/water nanoemulsion by sonicating or homogenizing; and b) administering the said nanoemulsion composition to human or animals.

The invention is now described by way of non-limiting examples. The invention comprises combinations of the embodiments and aspects of the invention as detailed herein. Accordingly, the invention also includes combinations and sub-combinations of the individual elements of the embodiments or aspects of the invention as described herein. Other features, advantages and embodiments of the invention will become apparent to those skilled in the art by the following description, accompanying examples. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention. A skilled artisan would realize that various changes and modifications may be made without diverting from the spirit of the invention.

EXAMPLE 1

Preparation of Nanoemulsion Using Soybean Oil and without Active Ingredient

| Formula | Quantities: g |
|---|---|
| soy bean oil | 20.0 |
| egg lecithin | 7.2 |
| polysorbate 80 | 7.2 |
| sodium hydroxide | q.s. to pH 6-9 |
| Water for Injections | to 100 g |

All processing stages are carried out under nitrogen.

An aqueous oil-in-water nanoemulsion is prepared as follows:

1. An aqueous phase is prepared from Water for Injections, stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter, polysorbate 80, and egg lecithin, in a vessel. The mixture is stirred at a temperature of approximately 60° C. until all ingredients are dissolved.
4. The mixture is added to the aqueous phase.
5. This mixture is then mixed with a high shear mixer (Polytron PT3100) at 10,000 rpm for 5 minutes to obtain a coarse emulsion. The emulsion pH is adjusted to 6-9.
6. The mixture is then homogenized with a high pressure homogenizer (APV 2000) in the range of 5,000-30,000 psi until reaching desired particle size.
7. The resulting oil-in-water nanoemulsion is cooled, pH adjust to 6-9 if necessary, and then transferred into a filling vessel.
8. The emulsion is then filtered with 0.22 micron filter and filled into containers under nitrogen.

EXAMPLE 2

Preparation of Nanoemulsion of Soybean Oil and Loaded with Active Drug-cyclosporine

| Formula | Quantities: g |
|---|---|
| cyclosporine | 0.2 |
| soy bean oil | 20.0 |
| egg lecithin | 7.2 |
| polysorbate 80 | 7.2 |
| glycerol | 2.25 |
| sodium hydroxide | q.s. to pH 6-9 |
| Water for Injections | to 100 g |

All processing stages are carried out under nitrogen.

An aqueous oil-in-water nanoemulsion is prepared as follows:

1. An aqueous phase is prepared from glycerol, and Water for Injections. This mixture is stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter, cyclosporine, polysorbate 80, and egg lecithin, in a vessel. The mixture is stirred at a temperature of approximately 60° C. until all ingredients are dissolved.
4. The mixture is added to the aqueous phase.
5. This mixture is then mixed with a high shear mixer (Polytron PT3100) at 10,000 rpm for 5 minutes to obtain a coarse emulsion. The emulsion pH is adjusted to 6-9.
6. The mixture is then homogenized with a high pressure homogenizer (APV 2000) in the range of 5,000-30,000 psi until desired particle size is reached.
7. The resulting oil-in-water nanoemulsion is cooled, pH adjust to 6-9 if necessary, and then transferred into a filling vessel.
8. The emulsion is then filtered with 0.22 micron filter and filled into containers under nitrogen.

Keratoconjunctivitis sicca (KCS) or dry eye syndrome is an eye disease caused by eye dryness, which, in turn, is caused by either decreased tear production or increased tear film evaporation. It is found in humans and some animals. KCS is the most common eye disease affecting 5-6% of the population. Prevalence rises to 6-9.8% in postmenopausal women, and as high as 34% in the elderly. Inflammation occurring in response to tears film hypertonicity can be suppressed by topical immunosuppressants, such as cyclosporine. Accordingly, the formulations such as described in this example and below may be used to increase tear production in patients whose tear production is presumed to be suppressed due to ocular inflammation associated with keratoconjunctivitis sicca.

EXAMPLE 3

Preparation of Nanoemulsion of Soybean Oil/Medium Chain Triglyceride and Loaded with Active Drug-cyclosporine

| Formula | Quantities: g |
|---|---|
| cyclosporine | 0.2 |
| soy bean oil | 10.0 |
| Medium chain triglyceride | 10.0 |
| egg lecithin | 7.2 |
| Polysorbate 80 | 7.2 |
| glycerol | 2.25 |
| sodium hydroxide | q.s. to pH 6-9 |
| Water for Injections | to 100 g |

All processing stages are carried out under nitrogen.

An aqueous oil-in-water nanoemulsion is prepared as follows:

1. An aqueous phase is prepared from glycerol, and Water for Injections. This mixture is stirred and heated to a temperature of approximately 60° C.
2. The aqueous phase is passed through a 0.22 micron filter and charged to a mixing vessel.
3. Separately, an oil phase is prepared from soy bean oil and medium chain triglyceride (Migloyol 812) that has been passed through a 0.22 micron filter, cyclosporine, polysorbate 80, and egg lecithin, in a vessel. The mixture is stirred at a temperature of approximately 60° C. until all ingredients are dissolved.
4. The mixture is added to the aqueous phase.
5. This mixture is then mixed with a high shear mixer (Polytron PT3100) at 10,000 rpm for 5 minutes to obtain a coarse emulsion. The emulsion pH is adjusted to 6-9 if necessary.
6. The mixture is then homogenized with a high pressure homogenizer (APV 2000) in range of 5,000-30,000 psi until reaching desired particle size.
7. The resulting oil-in-water nanoemulsion is cooled, pH adjust to 6-9 if necessary, and then transferred into a filling vessel.
8. The emulsion is then filtered with 0.22 micron filter and filled into containers under nitrogen.

EXAMPLE 4

Preparation of Nanoemulsion by Dilution from Example 1

| Formula | Quantities: g |
|---|---|
| soy bean oil | 5.0 |
| egg lecithin | 1.8 |
| polysorbate 80 | 1.8 |
| sodium hydroxide | q.s. to pH 6-9 |
| Water for Injections | to 100 g |

All processing stages are carried out under nitrogen.

An aqueous oil-in-water nanoemulsion is prepared as follows:

1. Obtain nanoemulsion sample from Example 1
2. Dilute the emulsion with purified water at the ratio of 1:3 v/v and mix well 3. Adjust the dilution pH to 6-9 if necessary and mix well
4. The emulsion is then filtered with 0.22 micron filter and filled into containers under nitrogen.

EXAMPLE 5

Preparation of Nanoemulsion by Dilution from Example 2

| Formula | Quantities: g |
|---|---|
| cyclosporine | 0.05 |
| soy bean oil | 5 |
| polysorbate 80 | 1.8 |
| egg lecithin | 1.8 |
| glycerol | 2.25 |
| sodium hydroxide | q.s. to pH 6-9 |
| Water for Injections | to 100 g |

All processing stages are carried out under nitrogen.

An aqueous oil-in-water nanoemulsion is prepared as follows:

1. Obtain nanoemulsion sample from Example 2
2. Dilute the emulsion with water solution containing 2.25% glycerol at the ratio of 1:3 v/v and mix well
3. Adjust the dilution pH to 6-9 if necessary and mix well
4. The emulsion is then filtered with 0.22 micron filter and filled into containers under nitrogen.

EXAMPLE 6

Preparation of Nanoemulsion by Dilution from Example 3

| Formula | Quantities: g |
|---|---|
| cyclosporine | 0.05 |
| soy bean oil | 2.5 |
| Medium chain triglyceride | 2.5 |
| polysorbate 80 | 1.8 |
| egg lecithin | 1.8 |
| glycerol | 2.25 |
| sodium hydroxide | q.s. to pH 6-9 |
| Water for Injections | to 100 g |

All processing stages are carried out under nitrogen.

An aqueous oil-in-water nanoemulsion is prepared as follows:

1. Obtain nanoemulsion sample from Example 3
2. Dilute the emulsion with purified water containing 2.25% glycerol at the ratio of 1:3 v/v and mix well
3. Adjust the dilution pH to 6-9 if necessary and mix well
4. The emulsion is then filtered with 0.22 micron filter and filled into containers under nitrogen.

EXAMPLE 7

Preparation of Emulsion Using Soybean Oil and Lecithin

Comparative Example

| Formula | Quantities: g |
|---|---|
| soy bean oil | 20.0 |
| egg lecithin | 12 |
| glycerol | 2.25 |
| sodium hydroxide | q.s. to pH 6-9 |
| Water for Injections | to 100 g |

All processing stages are carried out under nitrogen.

An aqueous oil-in-water emulsion is prepared as follows:

1. An aqueous phase is prepared from glycerol, and Water for Injections. This mixture is stirred and heated to a temperature of approximately 60° C.
2. The aqueous phase is passed through a 0.22 micron filter and charged to a mixing vessel.
3. Separately, an oil phase is prepared from soy bean oil that has been passed through a 0.22 micron filter and egg lecithin, in a vessel. The mixture is stirred at a temperature of approximately 60° C. until all ingredients are dissolved.
4. The mixture is added to the aqueous phase.
5. This mixture is then mixed with a high shear mixer (Polytron PT3100) at 10,000 rpm for 5 minutes to obtain a coarse emulsion. The emulsion pH is adjusted to 6-9.
6. The mixture is then homogenized with a high pressure homogenizer (APV 2000) in the range of 5,000-30,000 psi until no more reduction in particle size.
7. The resulting oil-in-water nanoemulsion is cooled, pH adjust to 6-9 if necessary, and then transferred into a filling vessel.
8. The emulsion is then filtered with 0.45 micron filter and filled into containers under nitrogen.

EXAMPLE 8

Preparation of Emulsion Using Soybean Oil and Lecithin and Polysorbate 80

| Formula | Quantities: g |
|---|---|
| soy bean oil | 20 |
| egg lecithin | 12 |
| Polysorbate 80 | 2.4 |
| sodium hydroxide | q.s. to pH 6-9 |
| Water for Injections | to 100 g |

All processing stages are carried out under nitrogen.

An aqueous oil-in-water emulsion is prepared following that of Example 1. The intensity averaged mean particle size of the emulsion made by the said invention is 68 nm (D50) by dynamic light scattering meter

EXAMPLE 9

Preparation of Emulsion Using Soybean Oil and Lecithin and Polysorbate 80

| Formula | Quantities: g |
| --- | --- |
| soy bean oil | 35.0 |
| egg lecithin | 2.52 |
| Polysorbate 80 | 12.6 |
| sodium hydroxide | q.s. to pH 6-9 |
| Water for Injections | to 100 g |

All processing stages are carried out under nitrogen.

An aqueous oil-in-water emulsion is prepared following that of Example 1. The intensity averaged mean particle size of the emulsion made by the said invention is 99 nm (D50) by dynamic light scattering meter

EXAMPLE 10

Preparation of Emulsion Using Soybean Oil and Lecithin and Poloxamer F68

| Formula | Quantities: g |
| --- | --- |
| soy bean oil | 13.3 |
| egg lecithin | 4.8 |
| Poloxamer F68 | 4.8 |
| Glycerol | 6.7 |
| sodium hydroxide | q.s. to pH 6-9 |
| Water for Injections | to 100 g |

All processing stages are carried out under nitrogen.

An aqueous oil-in-water emulsion is prepared following that of Example 1. The intensity averaged mean particle size of the emulsion made by the said invention is 67 nm (D50) by dynamic light scattering meter

EXAMPLE 11

Preparation of Emulsion Using Soybean Oil and Lecithin and Polysorbate 80

| Formula | Quantities: g |
| --- | --- |
| soy bean oil | 5.0 |
| egg lecithin | 3.0 |
| Polysorbate 80 | 0.6 |
| glycerol | 2.25 |
| sodium hydroxide | q.s. to pH 6-9 |
| Water for Injections | to 100 g |

All processing stages are carried out under nitrogen.

An aqueous oil-in-water emulsion is prepared by diluting nanoemulsion by Example 8 with glycerol solution. The intensity averaged mean particle size of the emulsion made by the said invention is 67 nm (D50) by dynamic light scattering meter.

EXAMPLE 12

Preparation of Emulsion Using Soybean Oil and Lecithin and Poloxamer F68

| Formula | Quantities: g |
| --- | --- |
| soy bean oil | 20.0 |
| egg lecithin | 7.2 |
| Poloxamer F68 | 1.27 |
| Glycerol | 10 |
| sodium hydroxide | q.s. to pH 6-9 |
| Water for Injections | to 100 g |

All processing stages are carried out under nitrogen.

An aqueous oil-in-water emulsion is prepared following that of Example 1. The intensity averaged mean particle size of the emulsion made by the said invention is 89 nm (D50) by dynamic light scattering meter

EXAMPLE 13

Preparation of Emulsion Using Soybean Oil and Lecithin and Poloxamer F68

| Formula | Quantities: g |
| --- | --- |
| soy bean oil | 20.0 |
| egg lecithin | 7.2 |
| Poloxamer F68 | 4 |
| Propylene glycol | 10 |
| sodium hydroxide | q.s. to pH 6-9 |
| Water for Injections | to 100 g |

All processing stages are carried out under nitrogen.

An aqueous oil-in-water emulsion is prepared following that of Example 1. The intensity averaged mean particle size of the emulsion made by the said invention is 75 nm (D50) by dynamic light scattering meter

EXAMPLE 14

Characterization of Nanoemulsion Size Distribution by Malvern Nano ZetaSizer

Figure 1:
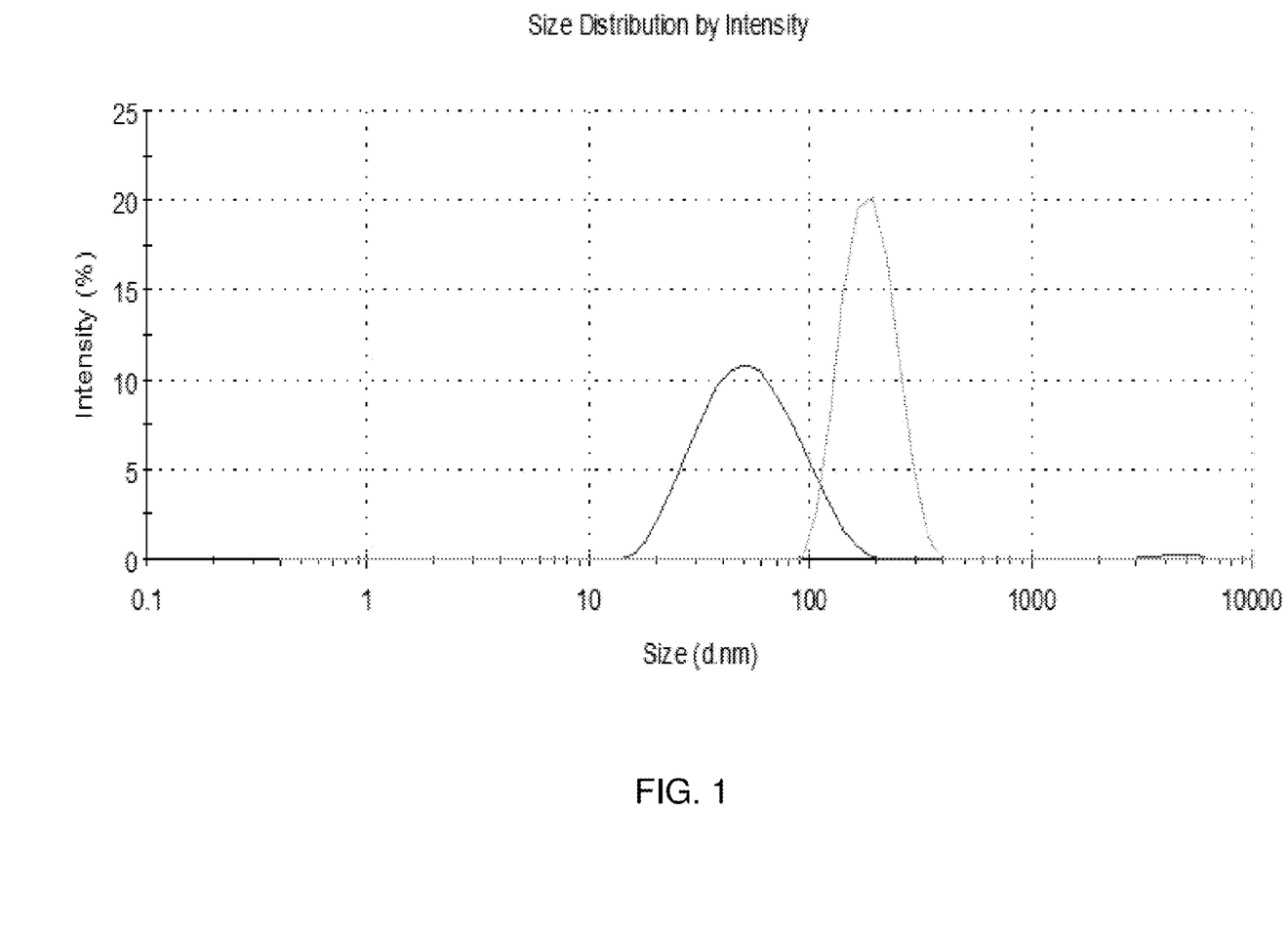
FIG. 1. Comparison of particle size distribution of nanoemulsion made with LCT/lecithin/polysorbate 80 (Example 1) vs macroemulsion made with only lecithin (Example 7). The average particle size of the nanoemulsion is 47 nm while the average of the macroemulsion is 177 nm.
Figure 2:
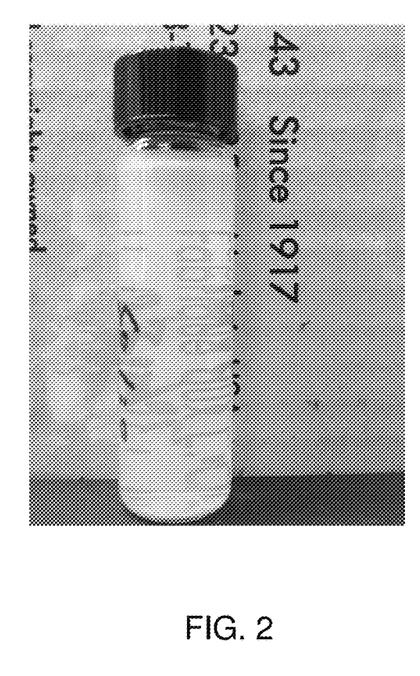
FIG. 2. Translucent nanoemulsion from Example 5.

The particle size distribution of the emulsion prepared with a single egg lecithin surfactant (Example 7) was compared again the emulsion prepared by the said invention (Example 1) (FIG. 1). The intensity averaged mean particle size of the emulsion made by the said invention is ~47 nm (D50), which is optically clear and has translucent appearance (FIG. 2), whereas, the one made with the soybean oil and with only egg lecithin surfactant (Example 7) has milky appearance and has intensity-averaged mean particle size of ~177 nm (D50).

EXAMPLE 15

Stability of Nanoemulsion Made with LCT/Lecithin and Polysorbate 80

Figure 3:
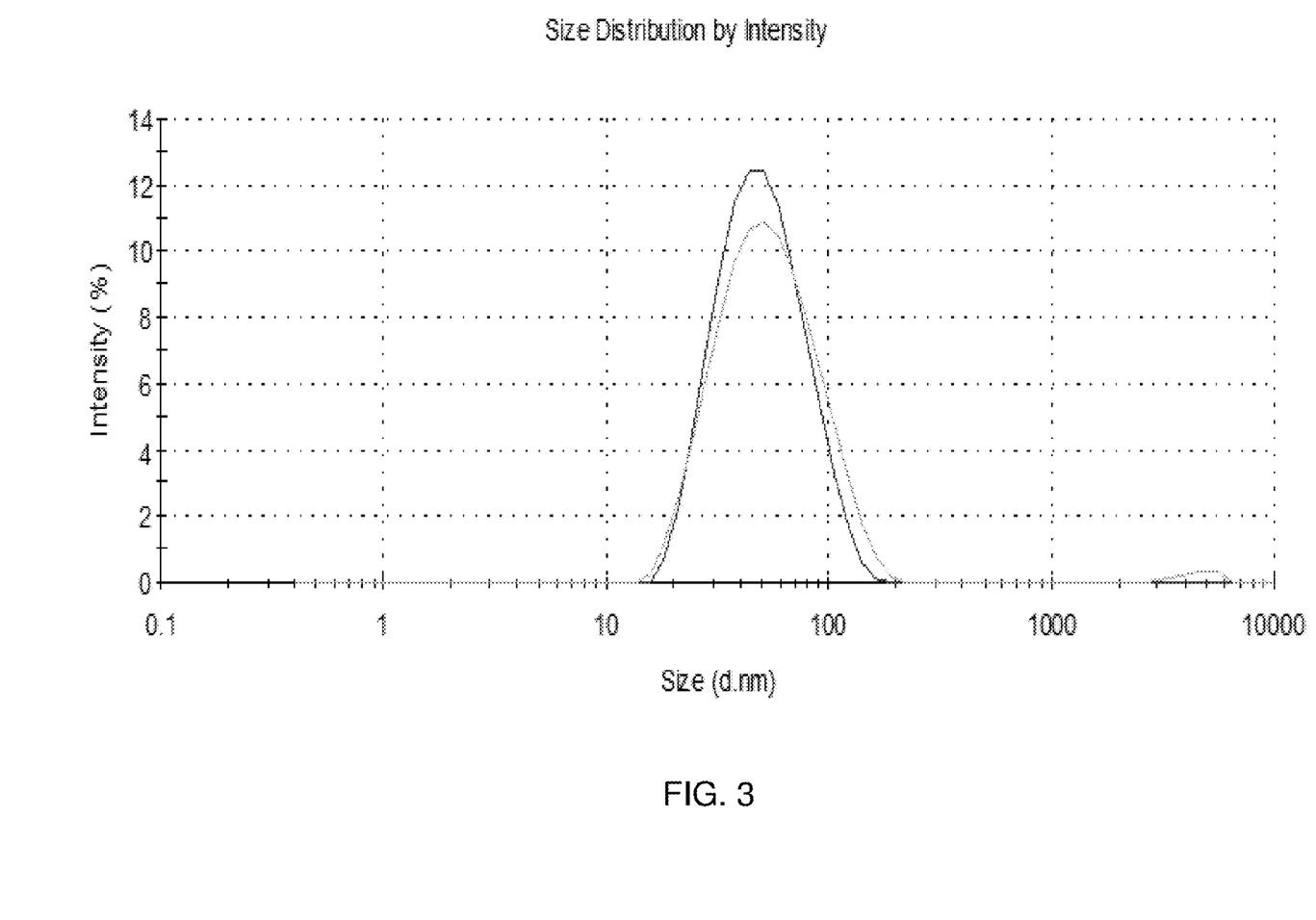
FIG. 3. Particle size distribution of nanoemulsion made with LCT/lecithin/polysorbate 80 (Example 1) after 5 months storage at 40° C./75% RH. The figure shows that the particle size distribution is almost same before and after the storage.

The particle size distribution of the emulsion prepared with lecithin/polysorbate 80 combination (Example 1) was monitored after stored at 40° C./75% RH for 5 months (FIG.

3). No change in particle size was observed after stability. The emulsion also maintained optically translucency after stability storage.

EXAMPLE 16

Figure 4:
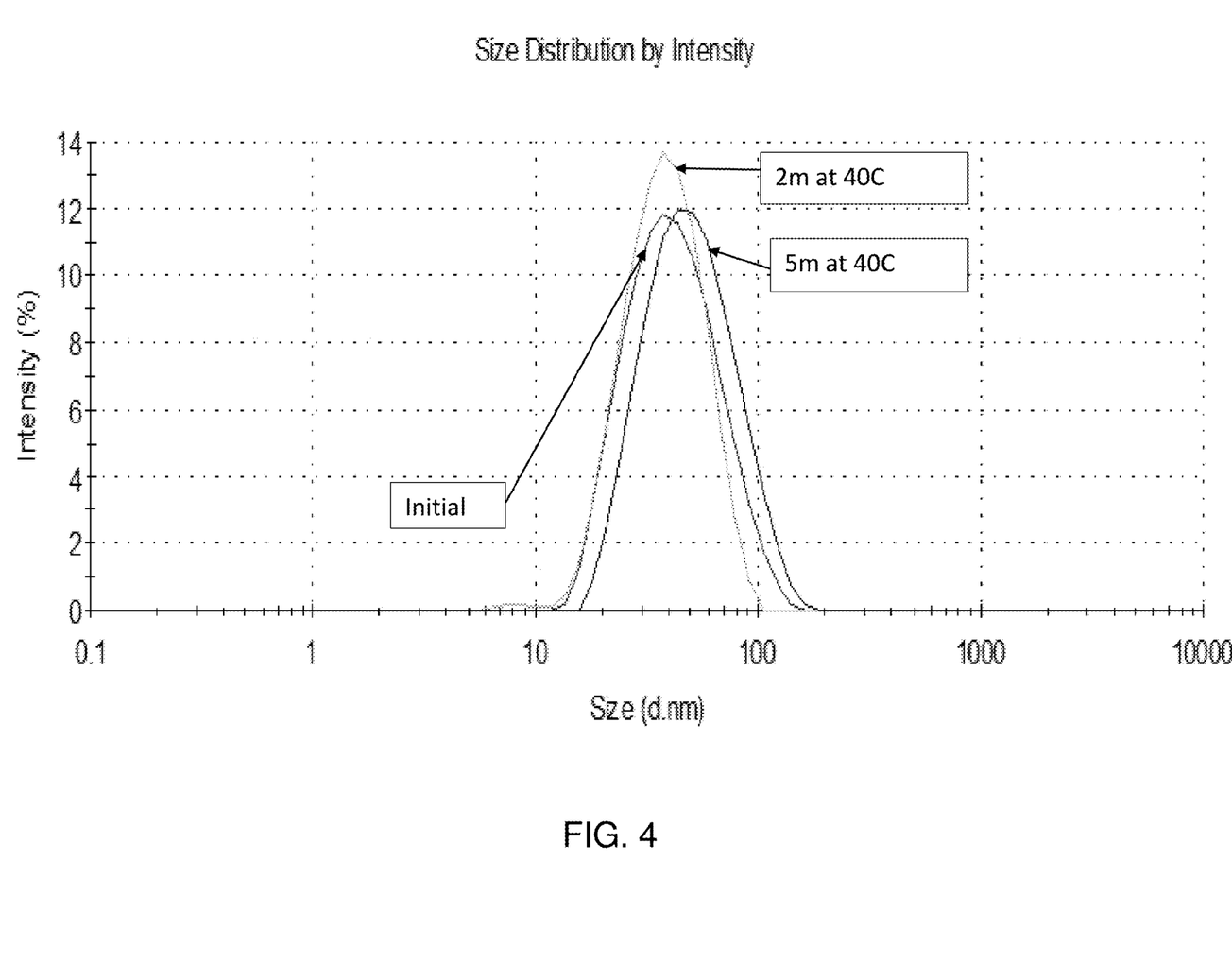
FIG. 4. Particle size distribution of nanoemulsion made with LCT/lecithin/polysorbate 80 and cyclosporine (Example 2) after 2 and 5 months storage at 40° C./75% RH. No significant change in particle size and optical clarity was observed. The average particle size was 38 nm for initial and 45 nm after 5 month at 40° C.

Stability of Nanoemulsion Made with LCT/Lecithin and Polysorbate 80 and Loaded with Active Component The particle size distribution of the emulsion prepared with lecithin/polysorbate 80 combination and active drug cyclosporine (Example 2) was monitored after stored at 40° C./75% RH for up to 5 months (FIG. 4). No significant change in particle size was observed after stability for up to 5 months. The average size is 38 nm for initial and 45 nm after 5 month at 40° C. The emulsion also maintained optically translucency and chemical stability of cyclosporine after stability storage.

|  | Initial | 3 months | 5 months |
| --- | --- | --- | --- |
| Assay (mg/mL) | 1.7 | 1.7 | 1.8 |
| D50 (nm) | 38 | 37 | 45 |

EXAMPLE 17

Figure 5:
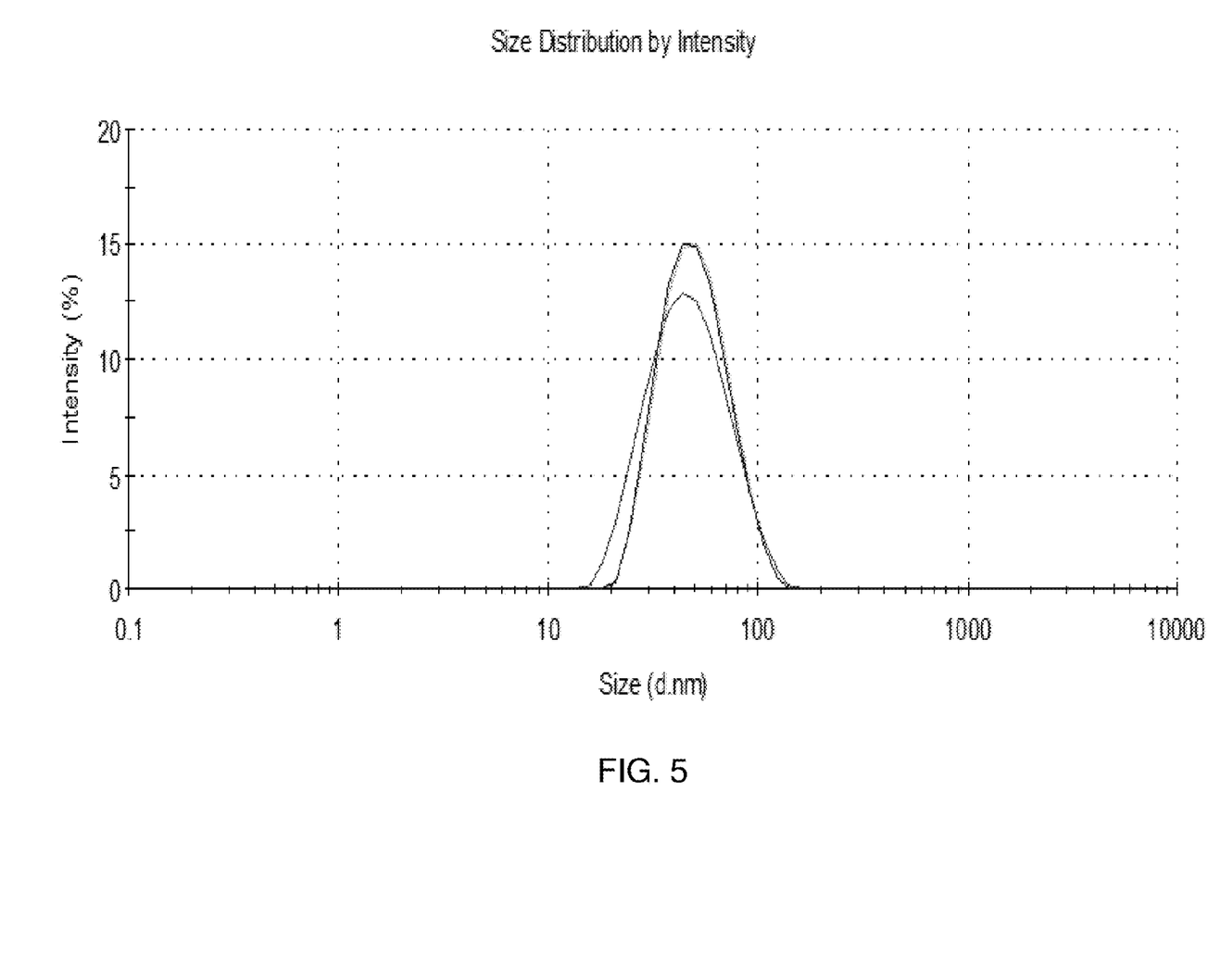
FIG. 5. Particle size distribution of nanoemulsion made with LCT/MCT/lecithin/polysorbate 80 and cyclosporine (Example 3) after 2 months storage at 40° C./75% RH.under refrigeration (~2-8° C.)/The figure shows that the particle size distribution is almost same before and after storage.

Stability of Nanoemulsion Made with Oil Mixture, Lecithin, and Polysorbate 80 and Loaded with Active Component The particle size distribution of the emulsion prepared with LCT/MCT/lecithin/polysorbate 80 combination and active drug cyclosporine (Example 3) was monitored after stored at 40° C./75% RH and 2-8° C. for 2 months (FIG. 5). No change in particle size was observed after stability. The emulsion also maintained optically translucency after stability storage.

EXAMPLE 18

Figure 6:
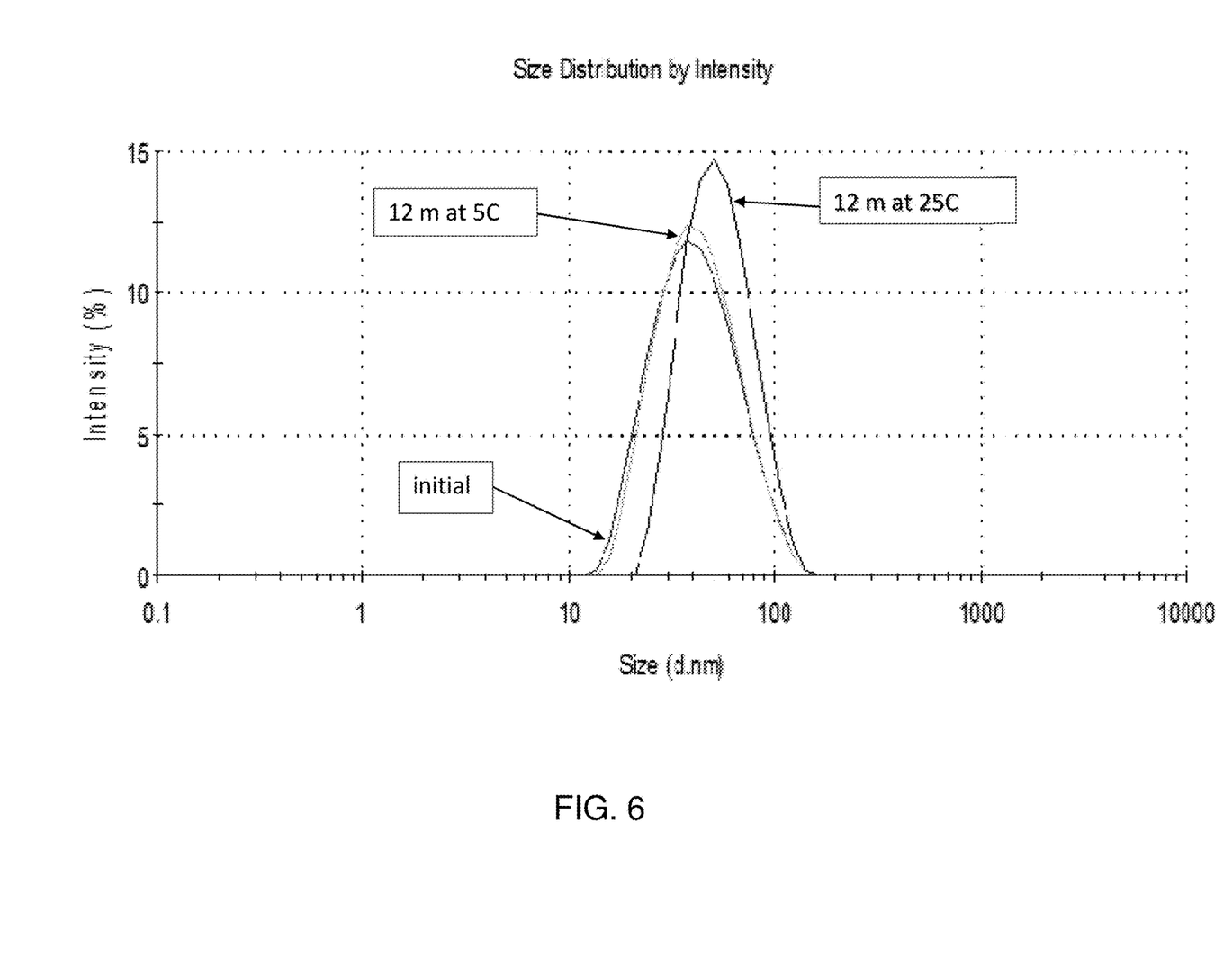
FIG. 6. Particle size distribution of nanoemulsion made with LCT/lecithin/polysorbate 80 and cyclosporine (Example 5) after 12 months storage at room temperature and refrigeration (~2-8° C.). No significant change in particle size and optical clarity was observed in either condition. The average particle size was 38 nm initially, 39 nm under refrigeration for 12 month, and 49 nm at 25° C. for 12 months.

Stability of Nanoemulsion Made with LCT Oil, Lecithin, and Polysorbate 80 and Loaded with Active Component The particle size distribution of the emulsion prepared with LCT/lecithin/polysorbate 80 combination and active drug cyclosporine (Example 5) was monitored after stored at controlled room temperature (~25° C.) and under refrigeration (~2-8° C.) for up to 14 months (FIG. 6). All mean particle size was observed to be below 50 nm after stability. The emulsion also maintained optically translucency and chemical stability for cyclosporine after stability storage.

|  | Initial | 14 month @5° C. | 14 months @25° C. |
| --- | --- | --- | --- |
| Assay (mg/mL) | 0.45 | — | 0.48 |
| D50 (nm) | 38 | 39 | 49 |

What is claimed is:

1. A stable, optically clear, oil-in-water nanoemulsion composition comprising:
    an oil phase comprising long chain triglyceride and/or other oils,
    wherein the composition comprises 0.5% to 50% (w/v) of the oil phase,
    the oil phase contains at least 10% (w/v) of the long chain triglyceride;
    an ionizable surfactant and co-surfactant(s),
    wherein the ionizable surfactant comprises 0.01% to 30% (w/v) of the composition, and
    wherein the co-surfactant(s) comprises 0.01% to 30% (w/v) of the composition;
    an aqueous phase containing no alcohol as the cosolvent;
    a pH adjusting agent; and
    an active component which is cyclosporine;
    wherein the mean droplet size (intensity-average, nm) of the composition is below 100 nm;
    wherein said droplets demonstrate stability for at least two months at 40° C./75% RH;
    and wherein the composition contains no alcohol.
2. The composition of claim 1, wherein the composition additionally comprises one or more agents selected from the group consisting of active component(s), a chelate agent, an antioxidant, an osmotic agent, a preservative, a suspending agent, and a buffering agent.
3. The composition of claim 1, wherein the mean droplet size (intensity-average, nm) is below 75 nm.
4. The composition of claim 1, wherein the oil phase is selected from soy bean oil, safflower seed oil, olive oil, cottonseed oil, sunflower oil, fish oil, castor oil, sesame oil, peanut oil, corn oil, medium chain triglycerides, or mixtures thereof.
5. The composition of claim 1, wherein the total weight of the surfactant and the co-surfactant is less than or equal to 40%, or 36%, 30%, 20%, or 15% (w/v) of the composition.
6. The composition of claim 1, wherein the total weight of the surfactant and co-surfactant is less than or equal to that of the oil phase.
7. The composition of claim 1, wherein the ratio of the surfactant and the co-surfactant is in the range of 10:0.1 to 0.1:10, 10:1 to 1:10, 10:1 to 1:5, or 5:1 to 1:5.
8. The composition of claim 1, wherein the surfactant concentration is less than 30% or 21% w/v of the composition.
9. The composition of claim 1, wherein the surfactant is selected from the group of pharmaceutically acceptable, biocompatible surfactants, comprising phospholipids extracted from egg yolk or soy bean, phospholipids derivatives, synthetic phosphatidyl cholines, purified phosphatidyl cholines from vegetable origin, or hydrogenated phospholipid derivatives.
10. The composition of claim 9, wherein the surfactant is egg lecithin or soy lecithin.
11. The composition of claim 1, wherein the co-surfactant is selected from the group of pharmaceutically acceptable surfactants, comprising poloxamers, poloxamines; polyoxyethylene stearates, polyoxyethylene sorbitan fatty acid esters or sorbitan fatty acid esters; ionic surfactants including cholic acid and deoxycholic acid; surface active derivatives or salts; oleic acid, sodium oleate, cholic acid, sodium cholate, deoxycholic acid, deoxysodium cholate and a mixture thereof.
12. The composition of claim 11, wherein the cosurfactant is polysorbate 80.
13. The nanoemulsion according to claim 1, wherein the nanoemulsion further comprises at least one additional active component.
14. A carrier formulation comprising the nanoemulsion of claim 1.

15. The formulation according to claim 14 for use in pharmaceutical, food, cosmetic, and other applications by routes comprising oral, intravenous, subcutaneous, intra muscular, inhalation, nasal, topical, ocular, and transdermal.

16. The formulation according to claim 14, in which the amount of active component is less than 50% w/v of the formulation.

17. The formulation of claim 14 for increasing tear production in patients whose tear production is presumed to be suppressed due to ocular inflammation associated with keratoconjunctivitis sicca.

18. A method to make a stable, optically clear, oil in water nanoemulsion composition according to claim 1, comprising long chain triglyceride with intensity-averaged oil droplets<100 nm without alcohol as cosolvent in the aqueous phase, said method comprising the steps of:
   a) preparing an oil phase comprising long chain triglyceride;
   b) preparing an aqueous phase comprising water and optionally other ingredients;
   c) incorporating biocompatible surfactant and co-surfactant(s) either in the oil phase or in the aqueous phase;
   d) dispersing the oil phase in the aqueous phase to form a coarse emulsion;
   e) forming a final emulsion by sonicating, high pressure homogenizing, or high shear processing the emulsion of step d); and
   f) adjusting pH.

19. The method of claim 18, wherein in step a) the oil phase comprises long chain triglyceride and one or more active ingredients.

20. The method of claim 18, wherein the aqueous phase of step b) includes pH adjustment agent, and one or more active ingredients are added into the final emulsion formed in step e).

21. The method of claim 18, wherein one or more active ingredients are added and mixed to dissolve in the coarse emulsion of step d).

* * * * *